(12) United States Patent
Hoshino

(10) Patent No.: US 10,194,878 B2
(45) Date of Patent: Feb. 5, 2019

(54) RADIATION IMAGING APPARATUS, RADIATION IMAGING SYSTEM, AND RADIATION IMAGING METHOD

(71) Applicant: CANON KABUSHIKI KAISHA, Tokyo (JP)

(72) Inventor: Mina Hoshino, Fujisawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 83 days.

(21) Appl. No.: 15/178,688

(22) Filed: Jun. 10, 2016

(65) Prior Publication Data
US 2016/0367211 A1  Dec. 22, 2016

(30) Foreign Application Priority Data
Jun. 19, 2015 (JP) .................................. 2015-124007

(51) Int. Cl.
*A61B 6/00* (2006.01)
(52) U.S. Cl.
CPC .................................. *A61B 6/5258* (2013.01)

(58) Field of Classification Search
CPC ....... A61B 6/541; A61B 6/542; A61B 6/5258; A61B 6/5205; A61B 6/545
See application file for complete search history.

(56) References Cited

U.S. PATENT DOCUMENTS 7,415,097 B2     8/2008   Spahn
2016/0331340 A1*   11/2016   Mako ................... A61B 6/5258

FOREIGN PATENT DOCUMENTS

JP     2013-118983 A     6/2013

* cited by examiner

*Primary Examiner* — Don Wong
(74) *Attorney, Agent, or Firm* — Venable LLP

(57) ABSTRACT

Provided is a radiation imaging apparatus, which is configured to acquire radiation exposure image data and non-radiation exposure image data, including: a setting unit configured to set at least one of an order or a frequency of generating offset correction data in association with imaging modes; a correction data generation unit configured to generate the offset correction data associated with each of the imaging modes from the non-radiation exposure image data in the set order or at the set frequency; and an image processing unit configured to correct, with use of the offset correction data, image data that is acquired by imaging a subject.

9 Claims, 7 Drawing Sheets

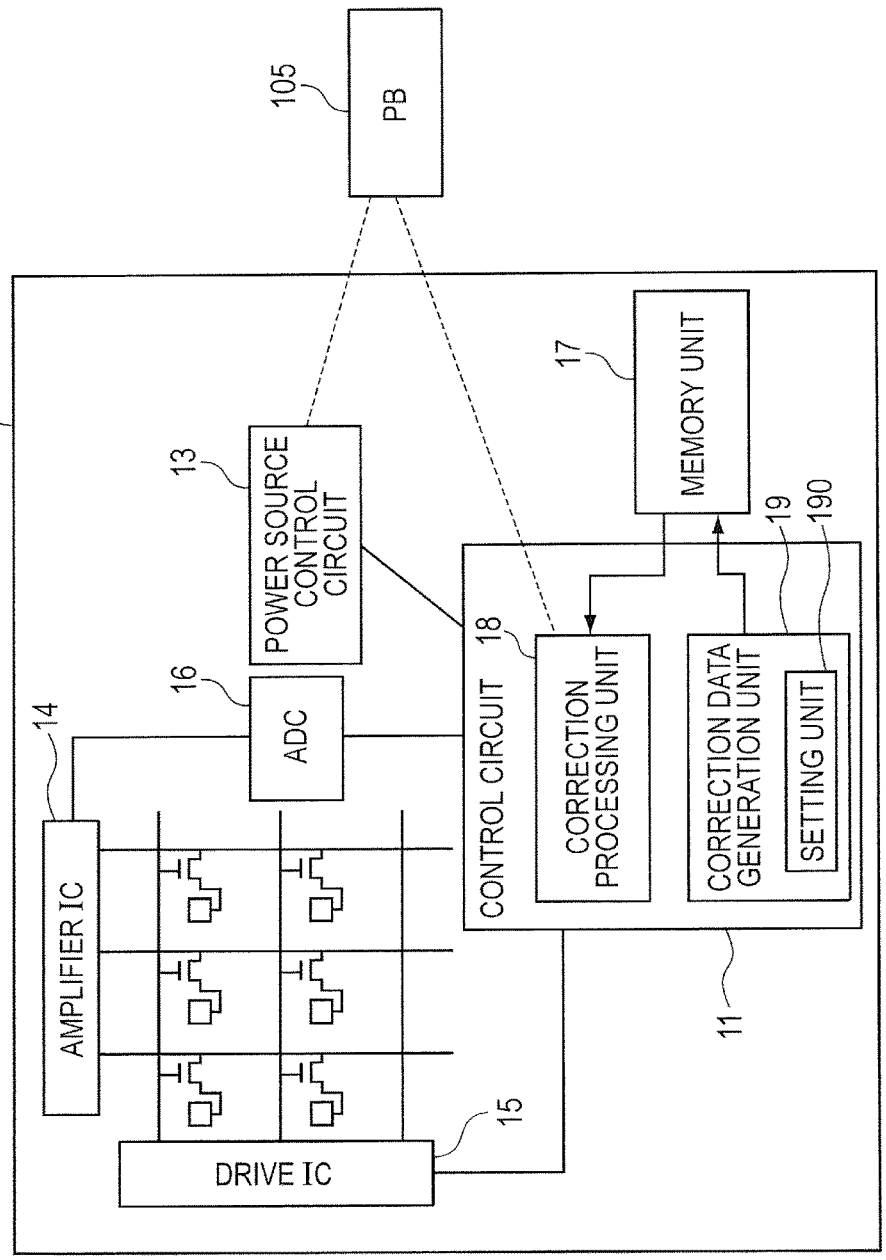

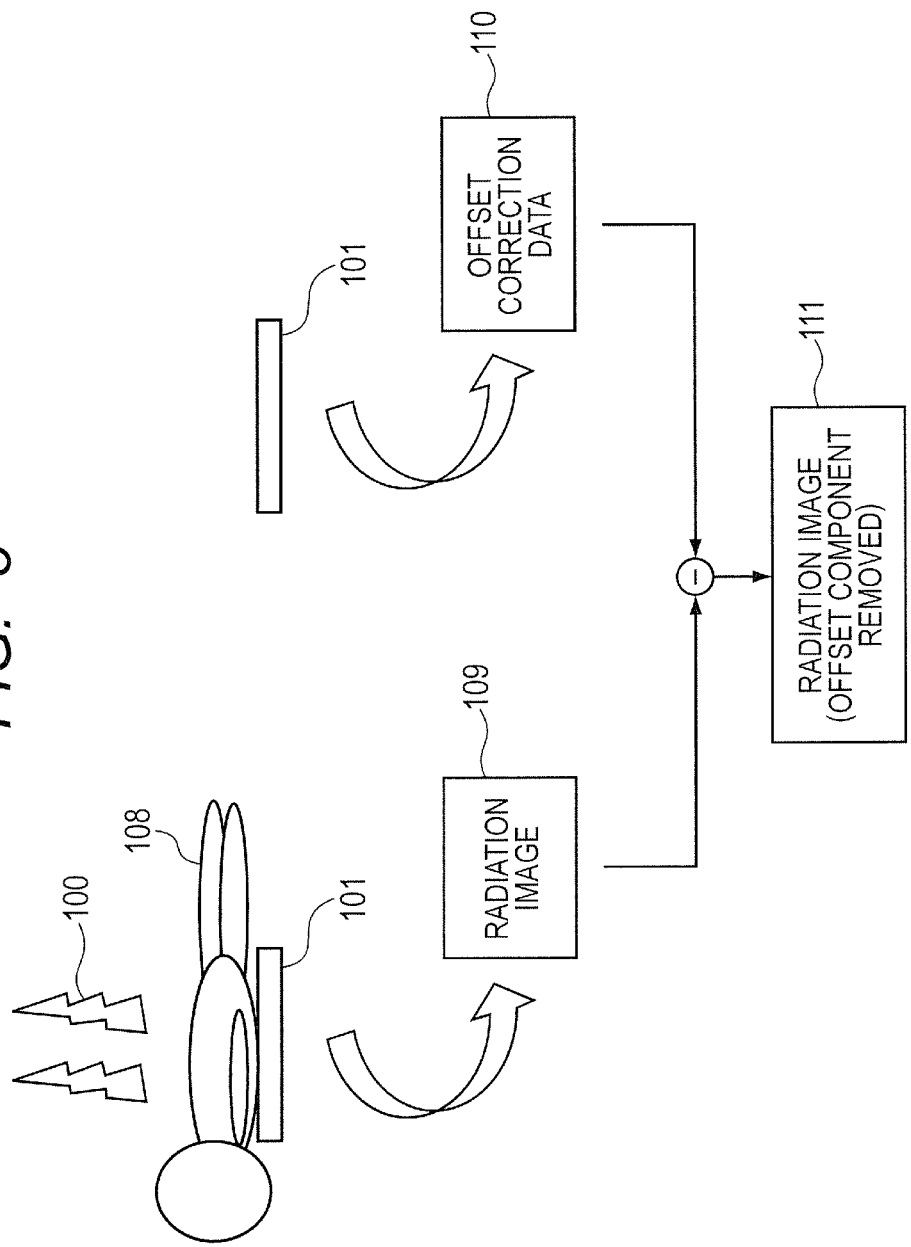

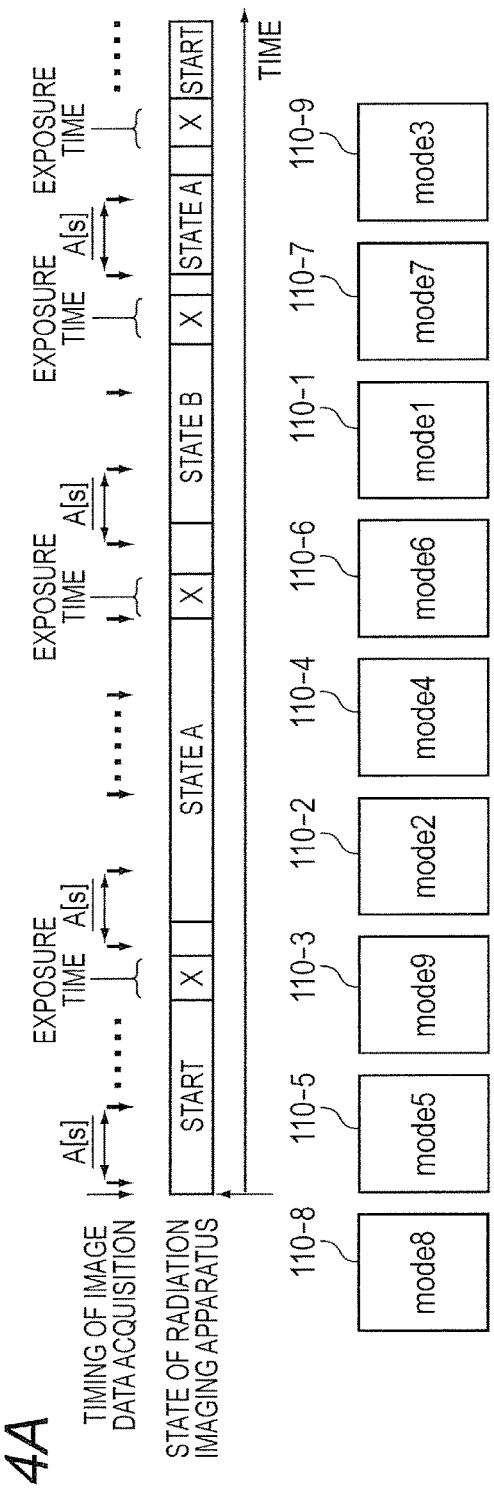
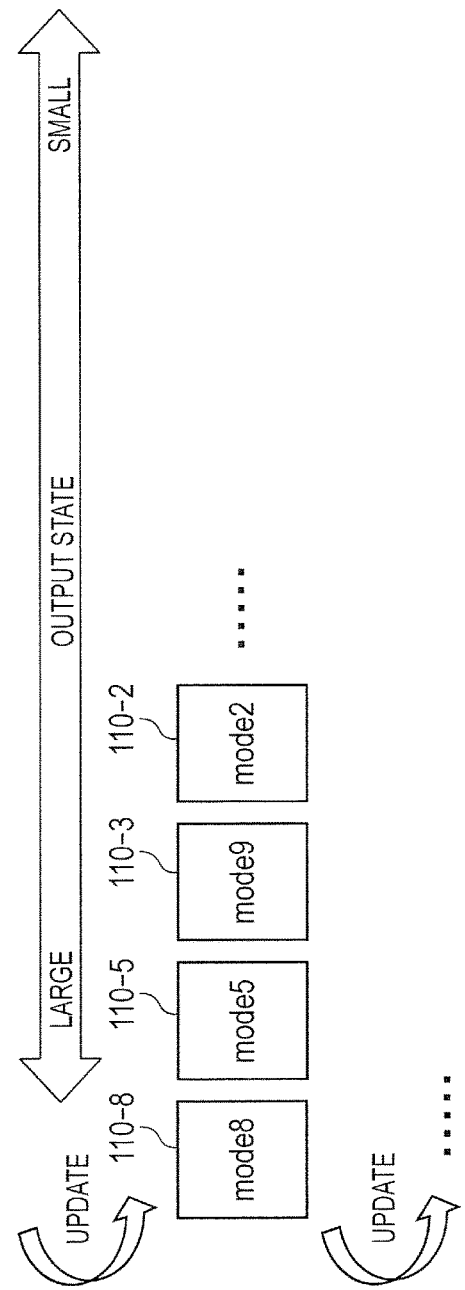
FIG. 4A
FIG. 4B

FIG. 5

| IMAGING MODE NUMBER | IMAGE SIZE | FRAME RATE [fps] | OUTPUT GAIN | ACQUISITION (UPDATE) ORDER |
|---|---|---|---|---|
| 1 | 43×43 | 15 | 2.0 | 7 |
| 2 | 43×43 | 30 | 3.5 | 4 |
| 3 | 43×43 | 3 | 1.0 | 9 |
| 4 | 30×30 | 15 | 3.0 | 5 |
| 5 | 30×30 | 30 | 4.5 | 2 |
| 6 | 30×30 | 3 | 2.5 | 6 |
| 7 | 15×15 | 15 | 1.5 | 8 |
| 8 | 15×15 | 30 | 5.0 | 1 |
| 9 | 15×15 | 3 | 4.0 | 3 |

FIG. 7

| IMAGING MODE NUMBER | IMAGE SIZE | FRAME RATE [fps] | OUTPUT GAIN | ACQUISITION (UPDATE) ORDER BASED ON OUTPUT GAIN | ACQUISITION (UPDATE) ORDER BASED ON OUTPUT GAIN AND FRAME RATE |
|---|---|---|---|---|---|
| 1 | 43×43 | 15 | 1.0 | 8 | 9 |
| 2 | 43×43 | 30 | 1.0 | 8 | 8 |
| 3 | 43×43 | 3 | 3.0 | 5 | 5 |
| 4 | 30×30 | 15 | 4.0 | 3 | 3 |
| 5 | 30×30 | 30 | 5.0 | 1 | 1 |
| 6 | 30×30 | 3 | 4.5 | 2 | 2 |
| 7 | 15×15 | 15 | 3.5 | 4 | 4 |
| 8 | 15×15 | 30 | 2.5 | 6 | 6 |
| 9 | 15×15 | 3 | 2.5 | 6 | 7 |

RADIATION IMAGING APPARATUS, RADIATION IMAGING SYSTEM, AND RADIATION IMAGING METHOD

BACKGROUND OF THE INVENTION

Field of the Invention

The present invention relates to a radiation imaging apparatus, a radiation imaging system, and a radiation imaging method for acquiring offset correction data.

Description of the Related Art

In recent years, imaging apparatus in which a radiation image is converted into digital signals directly and in real time are popular as imaging apparatus configured to capture a radiation image with radiation rays transmitted through an object. For an observation of the interior of a relatively large object, such as human body, in particular, large-area flat panel radiation imaging apparatus (flat panel displays: FPDs) have been proposed.

Capturing a radiation image involves offset correction processing in order to remove an offset component due to residual charge, dark current charge accumulated during photographing, or fixed-pattern noise.

Common offset correction processing is performed by using image data that is acquired without the irradiation of radiation rays (non-exposure image data) as offset correction data and subtracting the non-exposure image data from radiation image data.

In U.S. Pat. No. 7,415,097, the order (a sequence) in which correction-use images (correction frames, in particular, offset frames) for a plurality of operating modes are acquired is discussed. Offset frames for operating modes that are determined as high in the frequency of use in a particular time slot are updated preferentially in the subsequent time slot, and this operation is repeated continuously. The frequency of use is determined by weighted averaging, based on the length of use and the number of times recording operation is executed.

In Japanese Patent Application Laid-Open No. 2013-118983, the order in which the necessity/non-necessity of execution is determined for offset correction modes is varied depending on what testing technique is selected at the time of photographing. The length of time elapsed since the last execution time till the time of determination is measured for every offset correction mode. An offset correction mode for which the elapsed time exceeds a given length of time is determined as a mode that needs to be executed, and an offset correction mode for which the elapsed time is within the given length of time is determined as a mode that does not need to be executed.

As described above, radiation imaging apparatus have a possibility of image quality deterioration from an offset component that is caused by residual charge and dark current charge, or by fixed-pattern noise. It is therefore necessary to execute offset correction processing by acquiring non-exposure image data as offset correction data.

Offset correction data in this case needs to be acquired (or updated) for each of a plurality of imaging modes. A problem is that, when offset correction data is acquired (or updated) for every imaging mode, a long period of time is required until a radiation image of an object can be captured.

SUMMARY OF THE INVENTION

The present invention provides a radiation imaging apparatus capable of executing offset correction processing properly despite a limited length of time that can be spent on acquiring offset correction data.

According to one embodiment of the present invention, there is provided a radiation imaging apparatus, which is configured to acquire radiation exposure image data and non-radiation exposure image data, including: a setting unit configured to set at least one of an order or a frequency of generating offset correction data in association with given imaging modes; a correction data generation unit configured to generate the offset correction data associated with each of the imaging modes from the non-radiation exposure image data in the set order or at the set frequency; and an image processing unit configured to correct, with use of the offset correction data, image data that is acquired by imaging a subject.

Further features of the present invention will become apparent from the following description of exemplary embodiments with reference to the attached drawings.

BRIEF DESCRIPTION OF THE DRAWINGS

FIG. 2 is a diagram for illustrating an example of the configuration of a radiation imaging apparatus.

FIG. 3 is a diagram for schematically illustrating offset correction processing.

FIG. 4A and FIG. 4B are diagrams for illustrating how offset correction data is acquired and updated for each imaging mode.

FIG. 5 is a table for showing an example of imaging conditions of the imaging modes.

FIG. 7 is a table for showing an example of imaging conditions of the imaging modes.

DESCRIPTION OF THE EMBODIMENTS

An exemplary embodiment of the present invention is described in detail with reference to the drawings.

Figure 1:
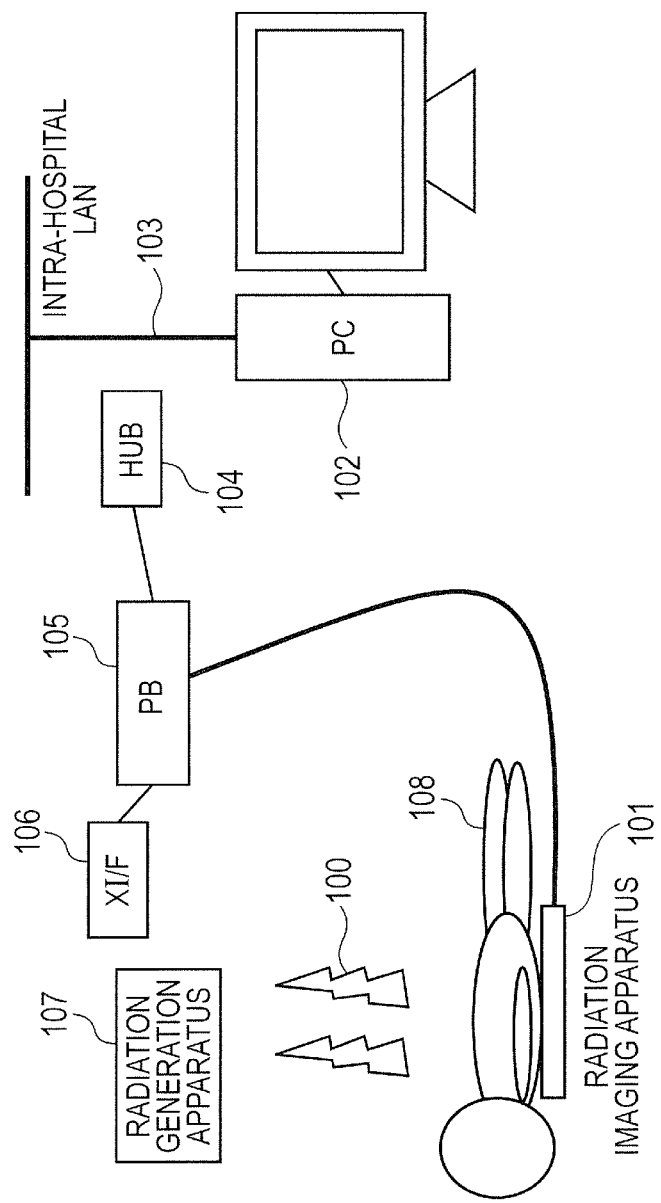
FIG. 1 is a diagram for illustrating an example of a radiation imaging system according to an embodiment of the present invention.

FIG. 1 is a diagram for illustrating an example of a radiation imaging system according to this embodiment. The radiation imaging system is used to, for example, capture a radiation image in a hospital. The radiation imaging system includes a radiation imaging apparatus 101, an electronic computer (personal computer: PC) 102, an intra-hospital LAN (a network installed inside a hospital) 103, a HUB 104, a power box (PB) 105, an X-ray interface box (XI/F) 106, and a radiation generation apparatus 107.

The radiation imaging apparatus 101 acquires radiation exposure image data by imaging an object that is being irradiated with radiation rays 100, and non-radiation exposure image data by imaging an object without the irradiation of the radiation rays 100. The image data acquired by the radiation imaging apparatus 101 is displayed on a display of the electronic computer 102. An imaging mode to be used for imaging by the radiation imaging apparatus 101 is input (instructed) through an input unit of the electronic computer 102.

The power box 105 supplies power to the radiation imaging apparatus 101 and other components. The X-ray interface box 106 holds a circuit configured to mediate communication to monitor the state of the radiation imaging apparatus 101, and control the irradiation of the radiation rays 100, the imaging operation, and the like, via the power box 105 and the radiation generation apparatus 107. The radiation generation apparatus 107 holds an X-ray tube and a rotor with which electrons are accelerated by a high voltage to collide against an anode in order to generate the radiation rays 100, and irradiates the radiation rays 100 onto the radiation imaging apparatus 101.

The radiation rays 100 emitted from the radiation generation apparatus 107 irradiate an object (patient) 108, and the radiation rays 100 that are transmitted through the object 108 are detected by the radiation imaging apparatus 101, thus generating a radiation image of the object 108. The radiation imaging apparatus 101 selects a given imaging mode from among a plurality of imaging modes as instructed by the electronic computer 102, and images the object 108 under imaging conditions of the selected imaging mode.

FIG. 2 is a diagram for illustrating an example of the configuration of the radiation imaging apparatus 101. The radiation imaging apparatus 101 includes a control circuit 11, a power source control circuit 13, an amplifier IC 14, a drive IC 15, an analog-digital converter (ADC) 16, and a memory (memory unit) 17. The control circuit 11 includes a correction processing unit (image processing unit) 18 and a correction data generation unit 19. The correction data generation unit 19 includes a setting unit 190.

A scintillator in the radiation imaging apparatus 101 absorbs the radiation rays 100 emitted from the radiation generation apparatus 107, and converts the radiation energy into light. Photoelectric conversion elements of the radiation imaging apparatus 101 convert the light into electric energy for electric accumulation.

The drive IC 15 selects a row in a photoelectric conversion element array and TFTs having a switching function switch on and off sequentially, to thereby read electric charges accumulated in the photoelectric conversion elements. The TFTs, which are thin film transistors, are made from an amorphous silicon film or the like formed on a glass substrate. The read charges are amplified by the amplifier IC 14, and the amplified analog data is converted into digital data by the ADC 16.

The control circuit 11 performs various types of processing on the digital data output from the ADC 16. The control circuit 11 holds communication to and from the electronic computer 102 and the X-ray interface box 106 via the power box 105. The power source control circuit 13 controls power from the power box 105.

The correction processing unit (image processing unit) 18 executes offset correction processing in which an offset component is removed. The correction processing unit (image processing unit) 18 uses offset correction data to correct image data, which is acquired by imaging a subject. The correction data generation unit 19 generates, for each of a plurality of imaging modes, offset correction data that is associated with the imaging mode. The setting unit 190 sets an order in which, or a frequency at which, offset correction data is generated in association with a given imaging mode. The correction data generation unit 19 generates pieces of offset correction data associated with imaging modes from image data (for example, non-exposure image data) in the order, or at the frequency, set by the setting unit 190.

The generated offset correction data is stored in the memory 17, and offset correction data that is associated with an imaging mode in question is read out of the memory 17 when the correction processing unit 18 executes the offset correction processing.

FIG. 3 is a diagram for schematically illustrating the offset correction processing. The radiation rays 100 are irradiated, transmitted through the object 108, and detected by a radiation detector of the radiation imaging apparatus 101, and a radiation image 109 of the object 108 is thus acquired. The radiation image 109 prior to the offset correction processing includes an image component of the object 108 and an offset component (noise component). Offset correction data 110 is acquired from non-radiation exposure image data generated by capturing an image without the irradiation of the radiation rays 100 (no exposure). The offset correction data 110 includes the noise component but not the image component of the object 108.

The offset correction data 110 is generated for each imaging mode. The offset correction data 110 is an average of a plurality of pieces of non-exposure image data acquired by capturing an image in the same imaging mode. The correction data generation unit 19 generates a piece of offset correction data 110 by averaging a plurality of pieces of non-exposure image data, and generates one piece of offset correction data for each imaging mode. The correction data generation unit 19 updates pieces of offset correction data associated with the respective imaging modes in a given order or at a given frequency.

The correction processing unit 18 uses the offset correction data 110 to correct the radiation image (image data) 109, which is acquired by imaging the object 108. Specifically, the correction processing unit 18 executes the offset correction processing by subtracting the offset correction data 110 from the radiation image 109. A radiation image 111 of the object 108 in which the offset component (noise component) is removed from the radiation image 109 is acquired in this manner.

FIG. 4A and FIG. 4B are diagrams for illustrating how offset correction data is acquired and updated for each imaging mode. Non-exposure image data cannot be acquired while a radiation image is being captured by exposure to the radiation rays 100. The correction data generation unit 19 therefore acquires non-exposure image data at a given time interval A [s] in time slots excluding ones in which exposure to the radiation rays 100 takes place. In this case, non-exposure image data is acquired irrespective of whether the radiation imaging apparatus 101 is in a warm-up state (start-up state), a warm-up completed state, a temperature shifting state, or other states.

In FIG. 4A, X represents a radiation exposure state, "start", "state A", and "state B" represent states of the radiation imaging apparatus 101 such as a warm-up (start-up) state, a warm-up completed state, and a temperature shifting state. Non-exposure image data is acquired at the given time interval A [s] in other states than the radiation exposure state X in FIG. 4A.

The correction data generation unit 19 generates a piece of offset correction data 110 by averaging a plurality of pieces of image data (non-exposure image data) acquired at the time interval A [s] in the same imaging mode. The correction data generation unit 19 updates pieces of offset correction data associated with the respective imaging modes in a given order or at a given frequency.

In FIG. 4B, the radiation imaging apparatus 101 has nine imaging modes. Based on imaging conditions of the imaging modes, the setting unit 190 sets an order in which pieces of offset correction data are generated to Imaging Mode 8, Imaging Mode 5, Imaging Mode 9, Imaging Mode 2, Imaging Mode 4, Imaging Mode 6, Imaging Mode 1, Imaging Mode 7, and Imaging Mode 3. The correction data generation unit 19 then generates offset correction data 110-1 to offset correction data 110-9, which are associated with Imaging Mode 1 to Imaging Mode 9, respectively, in the set order from image data.

For instance, the correction data generation unit 19 generates the offset correction data 110-8 by acquiring a plurality of pieces of image data (non-exposure image data) in Imaging Mode 8 at the time interval A [s], and averaging the acquired pieces of image data. After acquiring the offset correction data 110-3, which is associated with Imaging Mode 3, in accordance with the set order, the correction data generation unit 19 again generates the offset correction data 110-8 associated with Imaging Mode 8, and updates the offset correction data 110-8. The correction data generation unit 19 repeatedly acquires (or updates) the offset correction data 110-1 to the offset correction data 110-9 in the set order in this manner.

When the radiation imaging apparatus 101 has a plurality of imaging modes, the radiation imaging apparatus 101 in some cases requires a stand-by time during which the offset correction data 110 is acquired for every imaging mode in order to be ready for any imaging mode selected. The radiation imaging apparatus 101 may also require a time till an update is made to the offset correction data 110 in the case where radiation rays are irradiated continuously for imaging and only a limited time can consequently be spent on acquiring non-exposure image data.

In this embodiment, the setting unit 190 sets at least one of order or frequency with regards to the acquisition (or update) of the offset correction data 110. The correction data generation unit 19 preferentially acquires (or updates) the offset correction data 110 that is highly needed, thereby accomplishing proper offset correction processing despite a limited time that can be spent on acquiring the offset correction data 110.

As a result, the stand-by time during which offset correction data is acquired (or updated) is shortened, which makes radiation imaging of an object much quicker. For example, in an emergency, a stand-by time from the starting of the radiation imaging apparatus 101 till the capturing of the radiation image 109 of the object 108 can be shortened.

The setting unit 190 sets at least one of order or frequency based on at least one of the output gain (amplification rate), image size, or frame rate of the imaging modes so that the offset correction data 110 that is highly needed is acquired (or updated) preferentially. Offset correction data that is highly needed is, for example, offset correction data associated with an imaging mode that is susceptible to artifact errors in an image due to changes with time.

Generally speaking, an image captured in an imaging mode that is large in output gain (charge amplification rate) is prone to changes due to environmental factors, and accordingly to artifact errors. The setting unit 190 therefore sets a higher value to at least one of the order or the frequency for an imaging mode that is larger in output gain (amplification rate). The setting unit 190 also sets a higher value to at least one of the order or the frequency for an imaging mode that is smaller in image size or higher in frame rate.

FIG. 5 is a table for showing an example of imaging conditions of Imaging Modes 1 to 9. In FIG. 5, an image size, a frame rate, and an output gain (amplification rate) are set as imaging conditions.

The image size is the size of an exposure image, a non-exposure image, an exposure moving image, or a non-exposure moving image that is acquired by the radiation imaging apparatus 101 (for example, a radiation image of the object 108). The frame rate is the number of frames of a moving image or the like that are acquired per unit time, and is expressed in units of frames per second [fps]. When the numerical value of the frame rate is larger, the time interval A [s] is shorter, the speed at which offset correction data is acquired is faster, and the update time is shorter. The output gain is the amplification rate of charges generated in the radiation detector of the radiation imaging apparatus 101, and is expressed as the ratio of amplification of each operating mode to amplification of Operating Mode 3, which is used as a reference, in terms of amplification rate.

In FIG. 5, an item "acquisition (update) order" is provided to indicate the order in which offset correction data is acquired (updated). A higher place in acquisition (update) order is set to an imaging mode that is higher in output gain, that is, an imaging mode that is susceptible to artifact errors. The image quality of the radiation image can be improved as a result.

The correction data generation unit 19 generates the offset correction data 110 from non-exposure image data acquired at the given time interval A [s], which is variable. Shortening the time interval A [s] reduces the update time. Lengthening the time interval A [s] raises the chance of acquiring non-exposure data by avoiding time slots in which exposure to the radiation rays 100 takes place. In view of running a radiation imaging apparatus in an actual medical practice setting, setting the time interval A [s] as a value that can be varied by the user is user-friendly.

The correction processing unit 18 reads, out of the memory 17, the offset correction data 110 that is associated with the same imaging mode as that of the radiation image 109 of the object 108, and subtracts the read offset correction data 110 from the radiation image 109, thereby executing the offset correction processing. The radiation image 111 of the object 108 which is the radiation image 109 minus the offset component (noise component) is thus acquired and displayed on the display of the electronic computer 102 or the like to be used for diagnosis and other uses.

By preferentially acquiring (or updating) the offset correction data 110 that is highly needed in this manner, proper offset correction processing is accomplished despite a limited length of time that can be spent on acquiring the offset correction data 110.

Figure 6A:
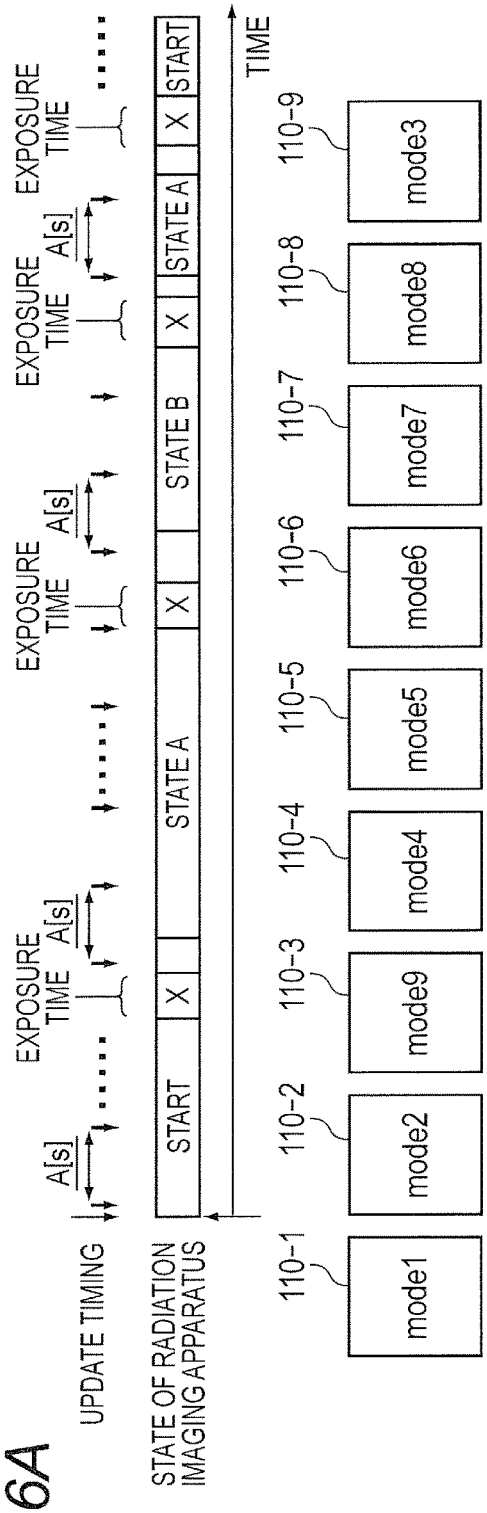
FIG. 6A and FIG. 6B are diagrams for illustrating how offset correction data is acquired and updated based on the priority of imaging conditions.
Figure 6B:
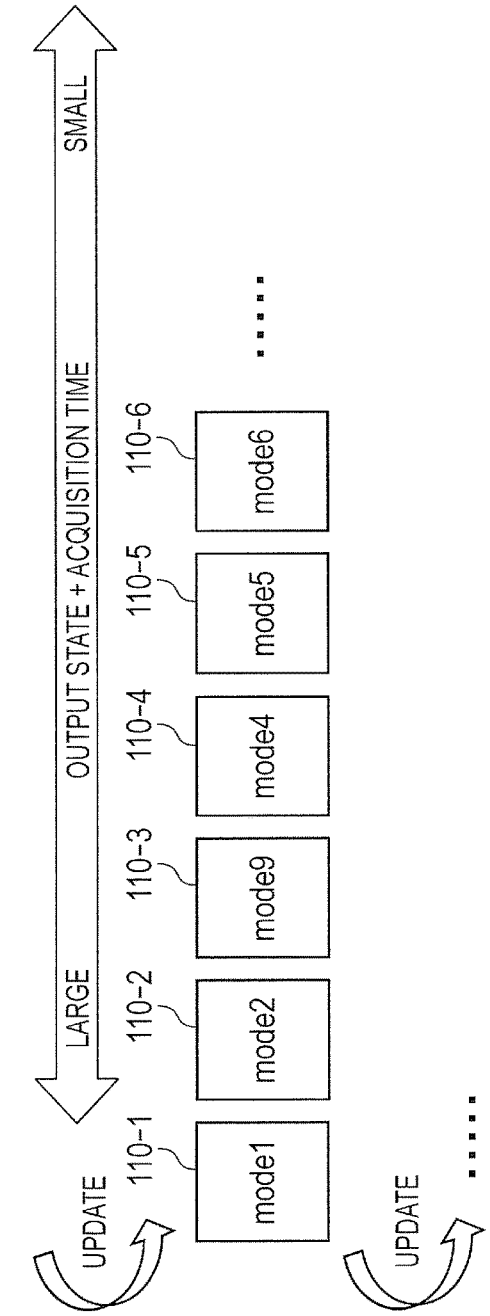

FIG. 6A and FIG. 6B are diagrams for illustrating how offset correction data is acquired and updated based on the priority of imaging conditions. The setting unit 190 determines the priority of at least two imaging conditions of the imaging modes, out of the output gain (amplification rate), the image size, or the frame rate, and sets at least one of order or frequency based on the determined priority.

FIG. 7 is a table for showing an example of imaging conditions of Imaging Mode 1 to Imaging Mode 9. The setting unit 190 in FIG. 7 sets the priority of the output gain higher than that of the frame rate, and sets the order in which the offset correction data 110 is acquired (updated) based on the output gain and the frame rate. In this case, a higher place in the acquisition (update) order is set for an imaging mode that is larger in output gain, and, in a case of imaging modes that have the same output gain value, one that is higher in frame rate than the other is set to a higher place in the acquisition (update) order.

The setting unit 190 may set a higher value to at least one of the order or frequency of generating the offset correction data 110 for an imaging mode that requires a shorter time to generate the offset correction data 110. Generally speaking, a shorter time is required to generate the offset correction data 110 when the image size is smaller or when the frame rate is higher. In this case also, a higher place in the acquisition (update) order may be set for an imaging mode that is larger in output gain, and, in a case of imaging modes that have the same output gain value, one that requires a shorter time to generate the offset correction data 110 than the other may be set to a higher place in the acquisition (update) order.

By preferentially acquiring (or updating) the offset correction data 110 that is generated in a short time, the number of pieces of offset correction data 110 that can be acquired within a given length of time is increased. Proper offset correction processing is accomplished as a result despite a limited length of time that can be spent on acquiring the offset correction data 110.

In FIG. 7, Imaging Modes 1 and 2 have the same output gain value, and the Imaging Modes 8 and 9 have the same output gain value. The time required to generate the offset correction data 110 is shorter for an imaging mode that is higher in frame rate in this case. Accordingly, Imaging Mode 2 is set to a higher place in order than that of Imaging Mode 1, and Imaging Mode 8 is set to a higher place in order than that of Imaging Mode 9. The time required to generate the offset correction data 110 is shorter also when the image size is smaller and reading that image takes an accordingly shorter time. A higher place in the order of acquiring (updating) the offset correction data 110 may therefore be set to an imaging mode that is smaller in image size out of imaging modes that have the same output gain value and the same frame rate value.

In this manner, the correction data generation unit 19 preferentially acquires (or updates) the offset correction data 110 that is highly needed based on a factor among imaging conditions that affects image quality adversely and a factor among imaging conditions that cuts short the time required to generate the offset correction data 110. Proper offset correction processing is accomplished as a result despite a limited length of time that can be spent on acquiring the offset correction data 110. In particular, by preferentially acquiring (or updating) the offset correction data 110 that is highly needed based on a factor that cuts short the time required to generate the offset correction data 110, imaging preparations can be completed for more imaging modes within a given length of time.

The setting unit 190 may set a factor that cuts short the time required to generate the offset correction data 110 (for example, the frame rate or the image size), instead of a factor that adversely affects image quality (for example, the output gain), to a priority level higher than the priority levels of other imaging conditions. Alternatively, the setting unit 190 may switch the priority level of a factor that adversely affects image quality and the priority level of a factor that cuts short the time required to generate the offset correction data 110.

The setting unit 190 may also set a frequency at which the offset correction data 110 is acquired (or updated) based on at least one of a factor among imaging conditions that affects image quality adversely or a factor among imaging conditions that cuts short the time required to generate the offset correction data 110. For example, the correction data generation unit 19 acquires (or updates) the offset correction data 110 twice in a given length of time for an imaging mode that has an output gain larger than a given threshold, and acquires (or updates) the offset correction data 110 once in the given length of time for an imaging mode that has an output gain smaller than the given threshold. The correction data generation unit 19 then repeats an update of the offset correction data 110 at the set frequency.

The correction data generation unit 19 may use at least one of order or frequency based on a factor among imaging conditions that affects image quality adversely to acquire (or update) the offset correction data 110, and then use at least one of order or frequency based on a factor among imaging conditions that cuts short the time required to generate the offset correction data 110, to acquire (or update) the offset correction data 110.

For instance, the correction data generation unit 19 acquires (or updates) the offset correction data 110 in an order based on the output gain, and then acquires (or updates) the offset correction data 110 in an order based on the frame rate. The correction data generation unit 19 subsequently switches the order based on the output gain and the order based on the frame rate in an alternating fashion.

In the case where an imaging condition to be used (for example, the image size) is specified in advance, the setting unit 190 may set at least one of the order or frequency of acquiring (or updating) the offset correction data 110 associated with an imaging mode that has the specified imaging condition.

For example, in the case where an image size "43×43" is specified in advance out of the imaging conditions of FIG. 5, an order in which pieces of offset correction data 110 that are associated with imaging mode numbers "1" to "3" are acquired (or updated) is set based on the output gain. The setting unit 190 may thus set at least one of the order or frequency of acquiring (or updating) the offset correction data 110 within a limited range of an imaging condition.

The correction data generation unit 19 may select one or more imaging conditions, or may switch from one imaging condition to another, as instructed by an input signal for selecting an imaging condition to be used in setting at least one of the order or frequency of acquiring (or updating) the offset correction data 110.

According to the present invention, proper offset correction processing is accomplished despite a limited time that can be spent on acquiring offset correction data, by setting the order or frequency of generating offset correction data based on an imaging condition.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-124007, filed Jun. 19, 2015, which is hereby incorporated by reference herein in its entirety.

What is claimed is:

1. A radiation imaging method for acquiring radiation exposure image data and non-radiation exposure image data, comprising:
   setting a frequency of generating offset correction data higher for an imaging mode that is higher in frame rate;
   generating the offset correction data associated with each of the imaging modes from the non-radiation exposure image data at the set frequency; and
   correcting, with use of the offset correction data, image data that is acquired by imaging a subject.

2. A radiation imaging apparatus, which is configured to acquire radiation exposure image data and non-radiation exposure image data, comprising:
   a setting unit configured to set at least one of an order or a frequency of generating offset correction data in association with imaging modes;
   a correction data generation unit configured to generate the offset correction data associated with each of the imaging modes from the non-radiation exposure image data in the set order or at the set frequency; and
   an image processing unit configured to correct, with use of the offset correction data, image data that is acquired by imaging a subject,
   wherein the setting unit is configured to set the at least one of the order or the frequency based on at least one of an amplification rate, an image size, or a frame rate of each of the imaging modes, and
   wherein the setting unit is configured to set a higher place in the order or to set the frequency higher for the imaging mode that is higher in amplification rate, smaller in image size, or higher in frame rate.

3. The radiation imaging apparatus according to claim 2, wherein the setting unit is configured to determine priority of at least two of an amplification rate, an image size, or a frame rate of each of the imaging modes, and to set the at least one of the order and the frequency based on the set priority.

4. A radiation imaging apparatus, which is configured to acquire radiation exposure image data and non-radiation exposure image data, comprising:
   a setting unit configured to set a frequency of generating offset correction data in association with a frame rate of each of imaging modes;
   a correction data generation unit configured to generate the offset correction data associated with each of the imaging modes from the non-radiation exposure image data at the set frequency; and
   an image processing unit configured to correct, with use of the offset correction data, image data that is acquired by imaging a subject,
   wherein the setting unit is configured to set the frequency higher for the imaging mode that is higher in frame rate.

5. The radiation imaging apparatus according to claim 4, wherein the correction data generation unit is configured to generate the offset correction data from the non-radiation exposure image data acquired at a given time interval, and
   wherein the time interval is variable.

6. The radiation imaging apparatus according to claim 4, wherein the setting unit is configured to set a higher place in the order or to set the frequency higher for an imaging mode that requires a shorter time to generate the offset correction data.

7. A radiation imaging system comprising:
   a radiation imaging apparatus configured to acquire radiation exposure image data and non-radiation exposure image data,
   the radiation imaging apparatus comprising:
      a setting unit configured to set a frequency of generating offset correction data in association with a frame rate of each of imaging modes;
      a correction data generation unit configured to generate the offset correction data associated with each of the imaging modes from the non-radiation exposure image data at the set frequency; and
      an image processing unit configured to correct, with use of the offset correction data, image data that is acquired by imaging a subject,
      wherein the setting unit is configured to set the frequency higher for the imaging mode that is higher in frame rate;
   a radiation generation unit configured to irradiate the radiation imaging apparatus with radiation rays; and
   an input unit for inputting one of the imaging modes.

8. The radiation imaging apparatus according to claim 2, wherein the offset correction data is stored in a memory, and the offset correction data that is associated with an imaging mode in question is read out of the memory when the image processing unit executes the offset correction processing.

9. The radiation imaging apparatus according to claim 8, wherein the offset correction data is acquired in a warm-up state of the radiation imaging apparatus.

* * * * *